US00PP08375P

United States Patent [19]

Button

[11] Patent Number: Plant 8,375

[45] Date of Patent: Sep. 14, 1993

[54] ANTHURIUM PLANT NAMED PURPLE VIKING

[76] Inventor: Richard J. Button, 1245 Obispo Ave., Coral Gables, Fla. 33134

[21] Appl. No.: 871,918

[22] Filed: Apr. 22, 1992

[51] Int. Cl.[5] ..... A01H 5/00
[52] U.S. Cl. ..... Plt./88.1
[58] Field of Search ..... Plt./88.1

*Primary Examiner*—James R. Feyrer
*Assistant Examiner*—Erich Veitenheimer
*Attorney, Agent, or Firm*—Foley & Lardner

[57] ABSTRACT

A new and distinct cultivar of Anthurium plant named Purple Viking, characterized by its unique relatively dark purple spathe, flowers which are held well above the foliage, shiny olive green foliage, and its floriferous habit.

1 Drawing Sheet

The invention relates to a new and distinct cultivar of Anthurium plant, botanically known as *Anthurium antigua,* and known by the cultivar name Purple Viking.

The new cultivar is a product of a planned breeding program carried out by the inventor, Richard J. Button, in Coral Gables, Fla. The cross resulting in the new cultivar was between parents which are unknown at this time. The new cultivar was discovered and selected by the inventor while growing among the progeny of the cross. Propagation by division was used to increase the number of plants for evaluation, and the stability of the combination of characters from generation to generation was clearly demonstrated.

The following observations, measurements and values describe plants grown in Homestead, Fla. under greenhouse conditions which closely approximate those generally used in horticultural practice.

The following traits have been repeatedly observed and have been repeatedly observed to be characteristics which in combination distinguish Purple Viking from other Anthuriums of the *A. antigua* type.

1. Purple Viking has a unique dark purple spathe.
2. The flowers are held well above the foliage.
3. Purple Viking has shiny olive green foliage which provides a striking contrast to the unique purple spathe color.
4. Purple Viking is very floriferous, having many spathe in bloom at the same time.

The accompanying color photograph illustrates in top perspective view the overall appearance of Purple Viking with several blossoms open and about to open. The photograph depicts color as true as possible in a color reproduction of this type.

All color references are to the Royal Horticultural Society Colour Chart. Colors are as closely approximate as possible since color, as well as other phenotypical characteristics, depends on horticultural practices such as light level, temperature and fertilization rate, among others, without, however, any variance in the genotype.

The following data are based on two plants grown in 10" pots. The plants were struck in week 20 of 1990 and grown a period of 69 weeks, with the data being accumulated in week 37 of 1991.

Origin: Seedling from unknown parents.
Classification: *A. antiqua,* c.v. Purple Viking.

Propagation: Asexual production either through tissue culture or division.

Plant: In a 10" pot when grown for the period indicated, the foliage of Purple Viking is approximately 40 cm in height (above soil line), and the total height to the top of the spathes is approximately 60 cm. The plant is approximately 68 cm in width. There are 5 breaks with one leaf expanded.

Leaves (2nd Expanded):
- *Length.*—25.5 to 27.5 cm.
- *Width.*—17 cm.
- *Length of base lobe from petiole to highest point on lobe.*—9 cm.
- *Tip.*—Acuminate.
- *Base.*—Truncate.
- *Margin.*—Entire, undulating.
- *Thickness.*—Medium.
- *Surface.*—Smooth.
- *Sheen.*—Very shiny.
- *Veins.*—Top, sunken; bottom, protruding; 3 primary lateral veins per side.
- *Shape.*—Between lateral veins at midpoint: convex with upturned edges. Longitudinal plane: Convex with downwardly turned tip. Transverse plane at tip: Sides generally downturned from midpoint.
- *Color.*—Mature: Top of leaf 137A, midrib 152A; bottom of leaf 146C, midrib 146D. Immature: Top of leaf darker than 143A, midrib 144A; bottom of leaf 148C, midrib 148D.

Petiole (2nd expanded leaf from apex):
- *Diameter.*—At top: 9 mm. Just below geniculum: 5 mm.
- *Distance.*—From petiole base to tip of wings: 4.5 cm. To base of geniculum: 26.5 cm. From top of wings to base of leaf: 24.6 cm.
- *Shape (at top of petiole wing).*—Emarginate.
- *Color.*—Mature 143C bottom, 146A top; immature, 143B-C top and bottom; wing, immature 145D, mature 145D base, 143C top.

Geniculum:
- *Diameter.*—6 mm.
- *Length.*—4 mm.
- *Color.*—mature, bottom 146C, top 146B; immature, 144A.

Inflorescence:
- *Pedicel length.*—43 cm.

*Spathe.*—Borne: The spathe is tightly rolled around the spadix and extrudes from the petiole sheath. The spathe is fully open when the pedicel is fully elongated. Length from tip to base: 14 cm. Width from tip to base: 10 cm. Cupping: Reflexed. Shape: Apex: Aristate to cuspidate; tip broken. Base: Cordate. Color: New (just after fully opening): Top 186B-C, bottom 186D; mature: Top 186C-D, bottom lighter than 186D. Time to flower: After 32 weeks for an untreated plant (depending on season), 1 to 3 blossoms will be present.

*Spadix.* Length: 7.5 cm. Width: 12 mm. Color: 183A when spathe unrolls, gradually changing.

*Pollen color.*—White.

*Pistil.*—Height 0.5 mm, color white.

*Stamens.*—Anthers and filaments are not clearly visible.

I claim:

1. A new cultivar and distinct cultivar of Anthurium plant named Purple Viking, as illustrated and described.

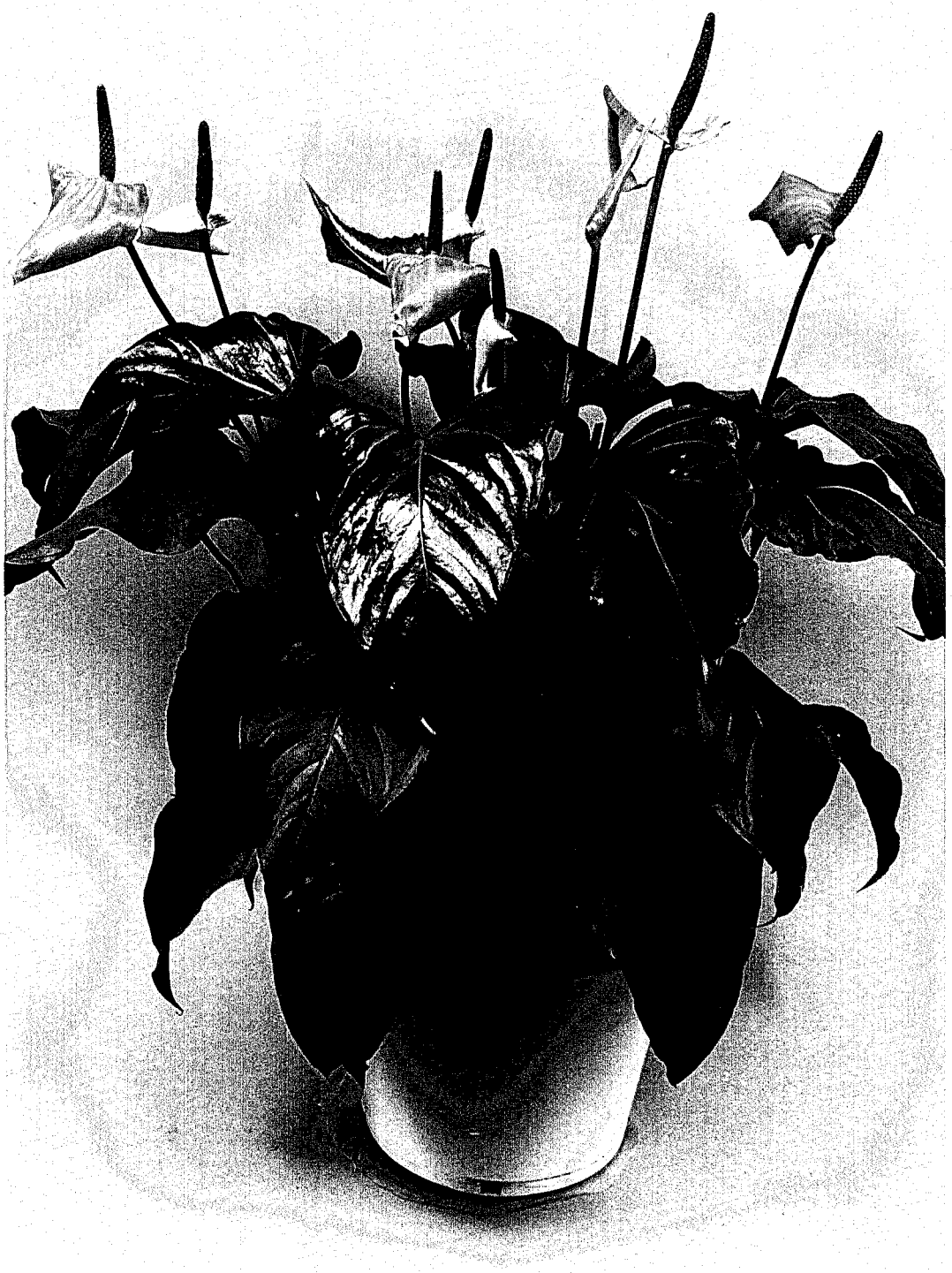

* * * * *